(12) United States Patent
Cistola et al.

(10) Patent No.: US 10,775,458 B2
(45) Date of Patent: Sep. 15, 2020

(54) METHOD AND SYSTEM FOR NON-INVASIVE MEASUREMENT OF METABOLIC HEALTH

(71) Applicant: Texas Tech University System, Lubbock, TX (US)

(72) Inventors: David P. Cistola, El Paso, TX (US); Vipulkumar Patel, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 157 days.

(21) Appl. No.: 15/911,728

(22) Filed: Mar. 5, 2018

(65) Prior Publication Data

US 2019/0271749 A1   Sep. 5, 2019

(51) Int. Cl.
| | |
|---|---|
| *G01R 33/44* | (2006.01) |
| *G01R 33/30* | (2006.01) |
| *A61B 5/00* | (2006.01) |
| *A61B 5/055* | (2006.01) |
| *G01R 33/383* | (2006.01) |
| *G01R 33/20* | (2006.01) |

(52) U.S. Cl.
CPC ............ *G01R 33/448* (2013.01); *A61B 5/055* (2013.01); *A61B 5/4866* (2013.01); *A61B 5/4872* (2013.01); *G01R 33/20* (2013.01); *G01R 33/30* (2013.01); *G01R 33/302* (2013.01); *G01R 33/383* (2013.01)

(58) Field of Classification Search
CPC ..... A61B 5/055; A61B 5/4866; A61B 5/4872; G01R 33/448; G01R 33/30; G01R 33/383; G01R 33/302; G01R 33/20
See application file for complete search history.

(56) References Cited

U.S. PATENT DOCUMENTS 5,072,732 A * 12/1991 Rapoport ............... A61B 5/055
                                                         324/308
5,320,103 A *  6/1994 Rapoport ............. G01R 33/383
                                                         324/318
(Continued)

FOREIGN PATENT DOCUMENTS

WO         9104744 A1    4/1991
WO         9110128 A1    7/1991
(Continued)

OTHER PUBLICATIONS

Barkemeyer, J. et al., Heteronuclear Polarization Transfer Using Selective Pulses during Hydrogenation with Parahydrogen, Journal of Magnetic Resonance, Series A (1996) 120:129-132.
(Continued)

*Primary Examiner* — Amy He
(74) *Attorney, Agent, or Firm* — Loza & Loza LLP; Kevin L. Soules

(57) ABSTRACT

A medical testing system comprises a housing, at least one magnet assembly configured around a probe configured to accept a human finger, formed in the housing wherein the at least one magnet assembly creates a permanent magnetic field around the probe, an RF signal generator configured to create a temporary magnetic field perpendicular to the permanent magnetic field in the housing, and an NMR coil assembly wherein a change in the permanent magnetic field induces a voltage in the NMR coil assembly.

20 Claims, 10 Drawing Sheets

(56) References Cited

U.S. PATENT DOCUMENTS

| | | |
|---|---|---|
| 5,343,389 A | 8/1994 | Otvos |
| 5,366,440 A | 11/1994 | Fossel |
| 6,426,058 B1 | 7/2002 | Pines et al. |
| 6,518,069 B1 | 2/2003 | Otvos et al. |
| 6,574,495 B1 | 6/2003 | Golman et al. |
| 6,576,471 B2 | 6/2003 | Otvos |
| 6,617,167 B2 | 9/2003 | Otvos et al. |
| 6,653,140 B2 | 11/2003 | Otvos |
| 6,683,455 B2 | 1/2004 | Ebbels et al. |
| 6,818,202 B2 | 11/2004 | Pines et al. |
| 7,191,069 B2 | 3/2007 | Wishart et al. |
| 7,243,030 B2 | 7/2007 | Reeve et al. |
| 7,306,562 B1 | 12/2007 | Baykal |
| 7,397,241 B2 | 7/2008 | Gauthausen et al. |
| 7,474,095 B2 | 1/2009 | Levitt et al. |
| 7,550,971 B2 | 6/2009 | Carpenter et al. |
| 7,564,243 B2 | 7/2009 | Desvaux et al. |
| 7,635,331 B2 | 12/2009 | Kim et al. |
| 7,647,234 B1 | 1/2010 | Ruderman et al. |
| 7,713,744 B2 | 5/2010 | Benner et al. |
| 7,750,633 B2 | 7/2010 | Pines et al. |
| 7,790,465 B2 | 9/2010 | Otvos |
| 7,940,045 B2 | 5/2011 | Carpenter et al. |
| 9,551,768 B2 | 1/2017 | Cistola et al. |
| 2002/0087276 A1 | 7/2002 | Otvos |
| 2003/0054599 A1 | 3/2003 | Huizing et al. |
| 2003/0119194 A1 | 6/2003 | Otvos |
| 2004/0098208 A1 | 5/2004 | Reeve et al. |
| 2004/0142496 A1 | 7/2004 | Nicholson et al. |
| 2005/0222504 A1 | 10/2005 | Otvos et al. |
| 2006/0104906 A1 | 5/2006 | Ardenkjaer-Larsen et al. |
| 2006/0164084 A1 | 7/2006 | Lomnes |
| 2006/0183234 A1 | 8/2006 | Otvos |
| 2007/0063700 A1 | 3/2007 | Levitt et al. |
| 2007/0178598 A1 | 8/2007 | Jeyarajah et al. |
| 2007/0264677 A1 | 11/2007 | Otvos |
| 2008/0038829 A1 | 2/2008 | Kremer et al. |
| 2008/0088308 A1 | 4/2008 | Carpenter et al. |
| 2008/0204014 A1 | 8/2008 | Desvaux et al. |
| 2009/0219022 A1 | 9/2009 | Carpenter et al. |
| 2010/0039109 A1 | 2/2010 | Cheng et al. |
| 2010/0100334 A1 | 4/2010 | Otvos |
| 2010/0219826 A1 | 9/2010 | Duckett et al. |
| 2010/0225316 A1 | 9/2010 | Jacob et al. |
| 2010/0233089 A1 | 9/2010 | Ross et al. |
| 2010/0308822 A1* | 12/2010 | Prado .................... G01N 24/08 324/309 |
| 2011/0160563 A1 | 6/2011 | Glogau et al. |
| 2012/0029340 A1 | 2/2012 | Does et al. |
| 2015/0018638 A1 | 1/2015 | Shames et al. |

FOREIGN PATENT DOCUMENTS

| | | |
|---|---|---|
| WO | 0017766 A2 | 3/2000 |
| WO | 0065366 A1 | 11/2000 |
| WO | 03012416 A1 | 2/2003 |
| WO | 2006076631 A2 | 7/2006 |
| WO | 2009129265 A1 | 10/2009 |
| WO | 2014071411 A1 | 5/2014 |
| WO | 2016127144 A1 | 8/2016 |

OTHER PUBLICATIONS

Bell, J. D. et al., Effects of n-3 fatty acids on the NMR provile of plasma lipoproteins, Journal of Lipid Research (1996) 37:1664-1674.

Bubici, S. et al. Inversion of Multi-component FFC-NMR relaxation decays, Stelar (2012) Sep. 26, 3 pages.

Choi, G. T. Y. et al., N.m.r. lipid profiles of cells, tissues and body fluids, Biochem. J. (1993) 290:717-721.

Cistola, D. P. et al., Compact NMR relaxometry of human blood and blood components, Trends in Analytical Chemistry (2016) 83:53-64.

Eaton, G. R. et al., Spin Lattice Relaxation in Solution and Summary of Relaxation Mechanisms, University of Denver Department of Chemistry and Biochemistr, Modern EPR Spectroscopy Euro-Summer School, Retie, Belgium, Dec. 1-2, 2002, 24 pages.

Hays, J. H. et al., Effect of a High Saturated Fat and No-Starch Diet on Serum Lipid Subfractions in Patients with Document Atherosclerotic Cardiovascular Disease, Mayo Clin. Proc. (2003) 78:1331-1336.

Mallol, R. et al., Human serum/plasma lipoprotein analysis by NMR: Application to the study of diabetic dyslipidemia, Progress in Nuclear Magnetic Resonance Spectroscopy (2013) 70:1-24.

Micklander, E. et al., Multivariate Analysis of Time Domain NMR Signals in Relation to Food Quality, Magnetic Resonance in Food Science: Latest Developments (2003) Belton et al. (eds) pp. 239-254.

Miller, W. G. et al., Seven Direct Methods for Measuring HDL and LDL Cholesterol Compared with Ultracentrifugation Reference Measurement Procedures, Clin. Chem. (2010) 56(6):977-986.

Mo, H. et al., Pre-SAT180, a Simple and Effective Method for Residual Water Suppression, J. Magn. Reson. (2008) 190(1):1-6.

Total Cholesterol Certification Protocol for Manufacturers—Revised, National Reference System for Cholesterol, Oct. 2004, 11 pages.

Robinson, M. D. et al., Nanofluidity of Fatty Acid Hydrocarbon Chains as Monitored by Benchtop Time-Domain Nuclear Magnetic Resonance, Biochemistry (2014) 53:7515-7522.

Spin-lattice relaxation—Wikipedia, printed Mar. 2, 2018, accessed Jan. 21, 2001, 3 pages.

Tang, H. et al., Use of relaxation-edited one-dimensional and two dimensional nuclear magnetic resonance spectroscopy to improved detection of small metabolites in blood plasma, Analytical Biochemistry (2004) 325:260-272.

\* cited by examiner

METHOD AND SYSTEM FOR NON-INVASIVE MEASUREMENT OF METABOLIC HEALTH

TECHNICAL FIELD

Embodiments are generally related to the field of medical devices. Embodiments are further related to the field of nuclear magnetic resonance (NMR). Embodiments are also related to methods, systems, and devices for measuring relaxometry signals. Embodiments are related to methods, systems, and devices for measuring metabolic health. Embodiments are further related to methods, systems, and devices further comprising a compact device optimized for non-invasively measuring NMR relaxometry signals from the distal segment of the human index finger.

BACKGROUND

Diabetes is a leading cause of disease, disability, and death in modern societies. In the U.S., approximately 10% of the population or 30 million people have diabetes. Worldwide, the prevalence is approximately 400 million, and is projected to increase to 600 million by 2035. In addition to the heavy health burden of diabetes and its complications, the financial costs are enormous: $245 billion per year in the U.S. and $1.3 trillion per year worldwide.

Type 2 is the major form of diabetes, accounting for more than 90% of all cases. Type 2 diabetes does not have a sudden onset, but develops insidiously over many years or even decades. The earliest stage consists of insulin resistance, often accompanied by lipid abnormalities and a pro-inflammatory, pro-coagulation state. Insulin resistance is associated with obesity, which causes adipose tissue inflammation. A healthy pancreas attempts to compensate for insulin resistance by secreting more insulin into the blood. This compensatory response keeps blood glucose levels in the normal range (<100 mg/dL). Thus, early insulin resistance is not detected by fasting glucose levels, the primary diabetes screening test used in medical clinics.

Over time, the heavy secretory demand caused by insulin resistance damages the insulin-secreting beta cells of the pancreas. Once insulin secretory capacity diminishes by 30-50%, the pancreas can no longer keep up, and fasting blood glucose levels become elevated. This stage is known as prediabetes, defined by fasting glucose levels of 100-124 mg/dL or hemoglobin A1C levels of 5.7-6.4%. In addition, elevated fasting glucose is one of five clinical criteria for metabolic syndrome, a condition that reflects poor metabolic health. Individuals with metabolic syndrome have a five-fold increased risk for type 2 diabetes and a 2-3-fold increased risk for atherosclerotic cardiovascular disease. Like prediabetes, the clinical criteria for metabolic syndrome fail to detect early-stage insulin resistance, where damage to the pancreas begins.

There are blood tests that, in principle, could be used to detect early-stage insulin resistance and its associated metabolic abnormalities. Examples include fasting insulin, lipid profiles, C-reactive protein, and others. However, the collection of multiple blood tests or blood panels is too expensive for routine screening of metabolic health. Health insurance companies do not cover the cost of metabolic panels for asymptomatic individuals with normal fasting glucose levels.

To overcome this barrier, a blood test has been developed that assesses metabolic health. PCT Application PCT/US2016/016906, filed Feb. 2, 2016, titled "Methods and tools for diagnosing insulin resistance and assessing health status using NMR relaxation times for water" describes a means for developing an inexpensive blood test for frontline health screening and monitoring. The test can be used for the diagnosis of insulin resistance syndrome, an early metabolic abnormality that leads to type 2 diabetes. The test analyzes the spin relaxation times ($T_2$ and/or $T_1$ or surrogates of $T_2$ and/or $T_1$) of water in plasma, serum, or whole blood using nuclear magnetic resonance (NMR). The blood samples however, must be obtained using a conventional needle stick or finger prick. PCT Application PCT/US2016/016906 is incorporated herein by reference in its entirety.

Nuclear Magnetic Resonance (NMR) techniques are used for various medical and analytical purposes. The term "NMR" can refer to a variety of diagnostic methods. There are many types of NMR methods and instruments and thousands of distinct NMR experiments have been conducted.

The three main categories are NMR spectroscopy, NMR imaging (currently known as magnetic resonance imaging or MRI), and NMR relaxometry. Spectroscopy generates molecular signatures of an atomic resolution, and imaging generates anatomical images with spatial resolution. These two categories of NMR usually require high-field or large bore magnets and complex, expensive instrumentation. Although based on the same fundamental physics, NMR relaxometry involves different instrumentation, methods, and derived measurables, compared with spectroscopy and imaging. Thus, different kinds of NMR are used in somewhat related but distinct areas of medical diagnosis, imaging, and treatment.

Another NMR relaxometry-based blood test is described in U.S. application Ser. No. 13/839,420, filed Mar. 15, 2013, titled "NMR method for monitoring changes in the core of lipoprotein particles in metabolism and disease." Unlike the PCT application referenced above, this application describes a method for directly measuring the properties of protein and lipoprotein elements in a sample, typically blood, rather than measuring water. The method includes the placing of a small volume of a blood sample into an NMR instrument tuned to measure a particular nucleus, applying a series of radiofrequency pulses with intermittent delays in order to measure spin-spin and/or spin-lattice relaxation time constants. While this represents an advance in NMR relaxometry-based blood testing, it also requires collection of a blood sample via a standard blood draw or needle stick. U.S. application Ser. No. 13/839,420 is incorporated herein by reference in its entirety.

In general, NMR imaging and spectroscopy methods are too expensive and too cumbersome to be carried out in outpatient point-of-care settings, such as a primary care practitioner's office. Moreover, current NMR relaxometry methods require blood samples by venipuncture or finger prick.

Further, when a particular test is difficult to carry out, must be carried out off-site, will take significant time to complete, or any combination thereof, the use of that test tends to be less frequent than tests that can be carried out quickly and easily at a location (e.g., a physician's office, small clinic, or hospital) where patients are typically located.

Accordingly, there is an unmet need for testing methods that can be used to identify metabolic health and help identify patients at risk for diabetes. By extension, a need exists for faster, simpler, and less expensive means for identifying and measuring characteristics that correlate to metabolic health.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the disclosed embodiments to provide a method, system, and apparatus for measuring metabolic health.

It is another aspect of the disclosed embodiments to provide a method and system for a nuclear magnetic resonance (NMR) based device for measuring metabolic health.

It is another aspect of the disclosed embodiments to measure relaxometry signals using an NMR based device.

It is another aspect of the disclosed embodiments to provide medical methods, systems, and apparatuses, comprising a compact device optimized for non-invasively measuring NMR relaxometry signals from a segment of a human finger.

The aforementioned aspects and embodiments can be achieved as described herein. In an embodiment, a medical testing system and method can comprise a housing, at least one magnet assembly configured around a probe configured to accept a human finger, formed in the housing wherein the at least one magnet assembly creates a permanent magnetic field around the probe, an RF signal generator configured to create a temporary magnetic field perpendicular to the permanent magnetic field in the housing, and an NMR coil assembly wherein a change in the permanent magnetic field induces a voltage in the NMR coil assembly.

The NMR coil assembly further comprises an NMR coil surrounding the probe and a coil base configured to hold the NMR coil.

The at least one magnet assembly further comprises a permanent magnet mounted in the housing externally to the probe. The permanent magnet further comprises a rare earth magnet. The at least one magnet assembly further comprises a yoke and a magnet pole shoe configured to disperse the permanent magnetic field.

The embodiments can further comprise a heater configured inside the housing wherein the heater maintains a temperature inside the housing. A computer system can be operably connected to the NMR device wherein the computer system provides an output indicative of a testing result.

BRIEF DESCRIPTION OF THE FIGURES

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

Figure 1:
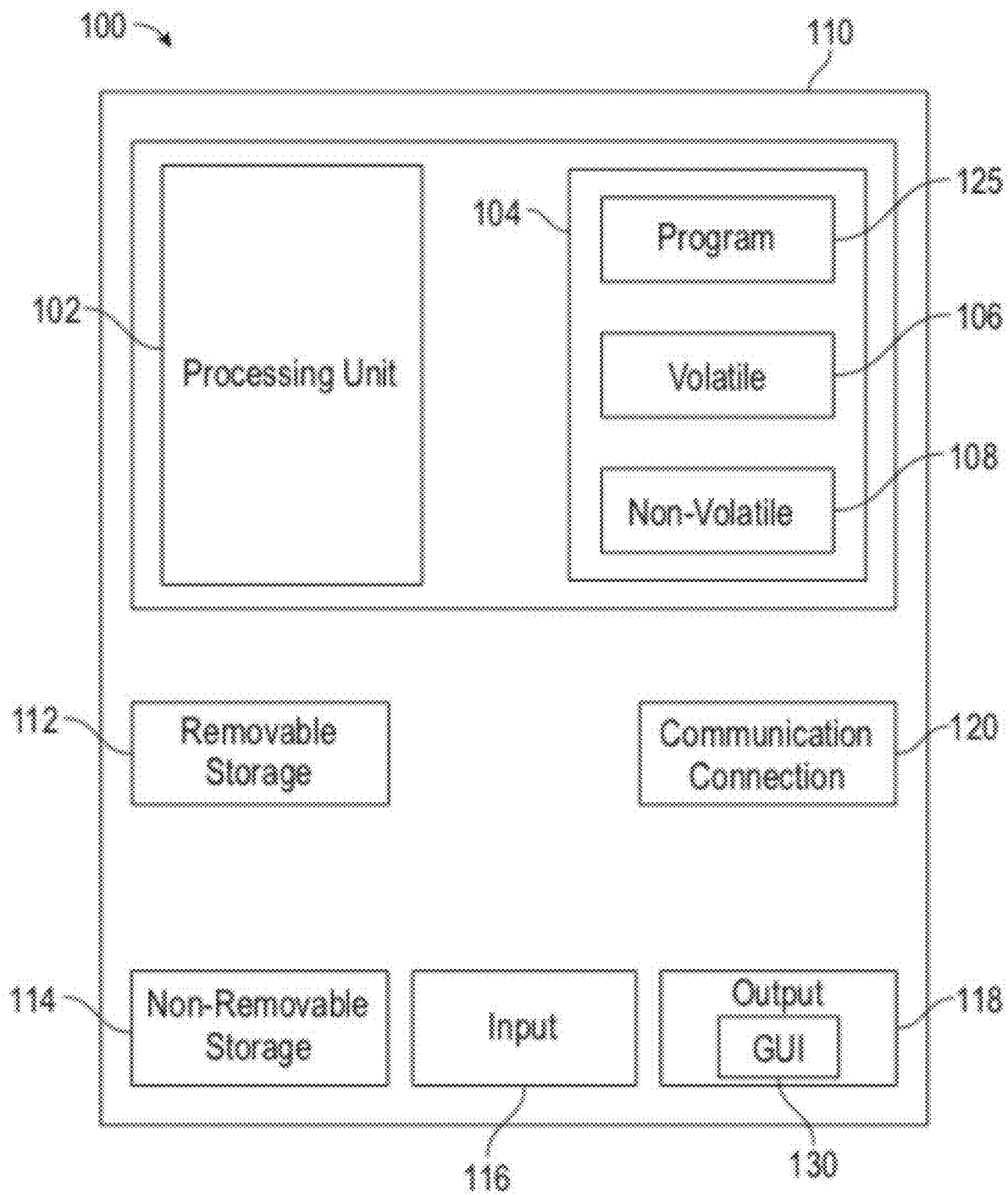
FIG. 1 depicts a block diagram of a computer system which is implemented in accordance with the disclosed embodiments.

The particular values and configurations discussed in the following non-limiting examples can be varied and are cited merely to illustrate one or more embodiments and are not intended to limit the scope thereof.

Example embodiments will now be described more fully hereinafter with reference to the accompanying drawings, in which illustrative embodiments are shown. The embodiments disclosed herein can be embodied in many different forms and should not be construed as limited to the embodiments set forth herein; rather, these embodiments are provided so that this disclosure will be thorough and complete, and will fully convey the scope of the embodiments to those skilled in the art. Like numbers refer to like elements throughout.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements, or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those skilled in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Figure 2:
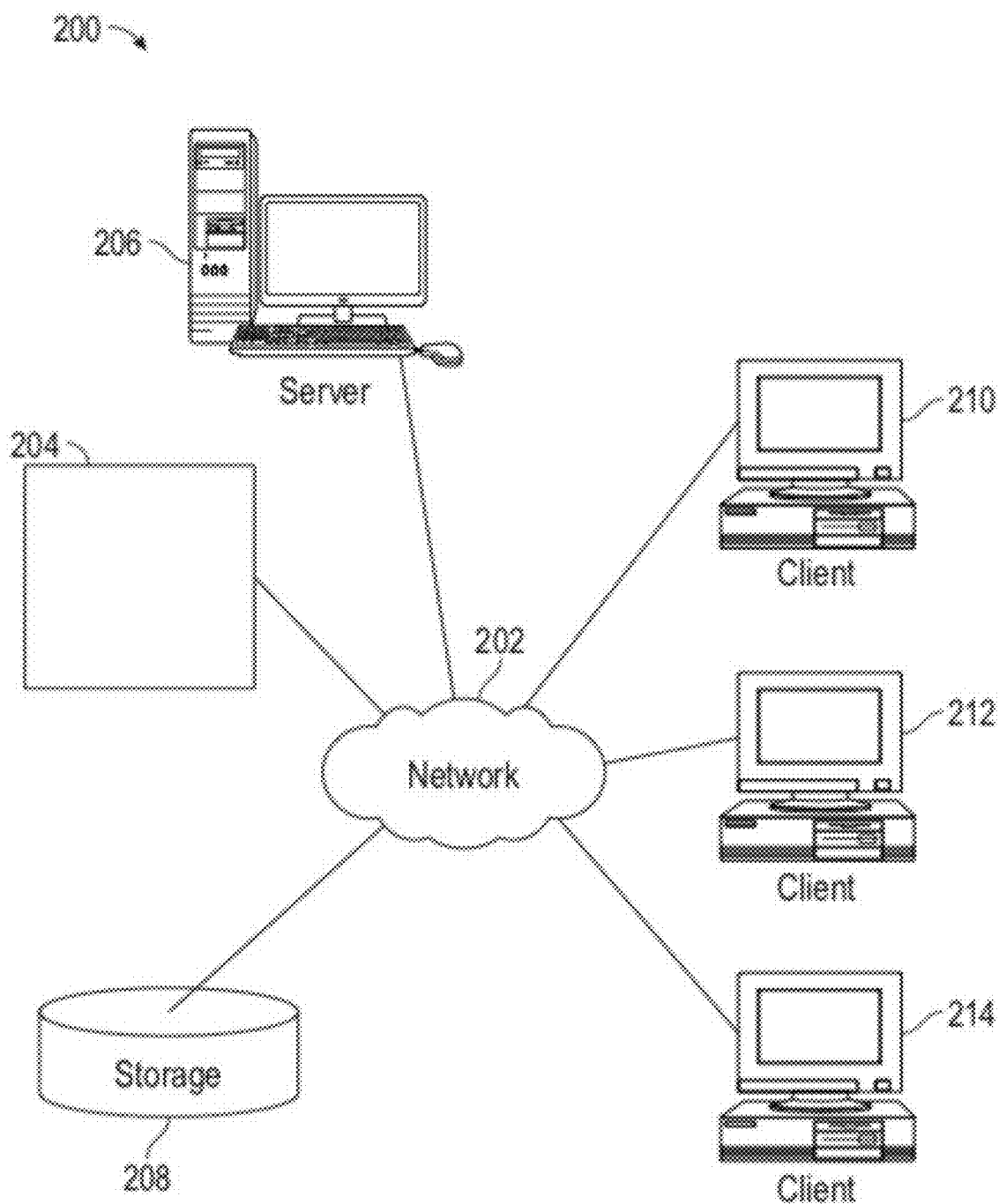
FIG. 2 depicts a graphical representation of a network of data-processing devices in which aspects of the present embodiments may be implemented.
Figure 3:
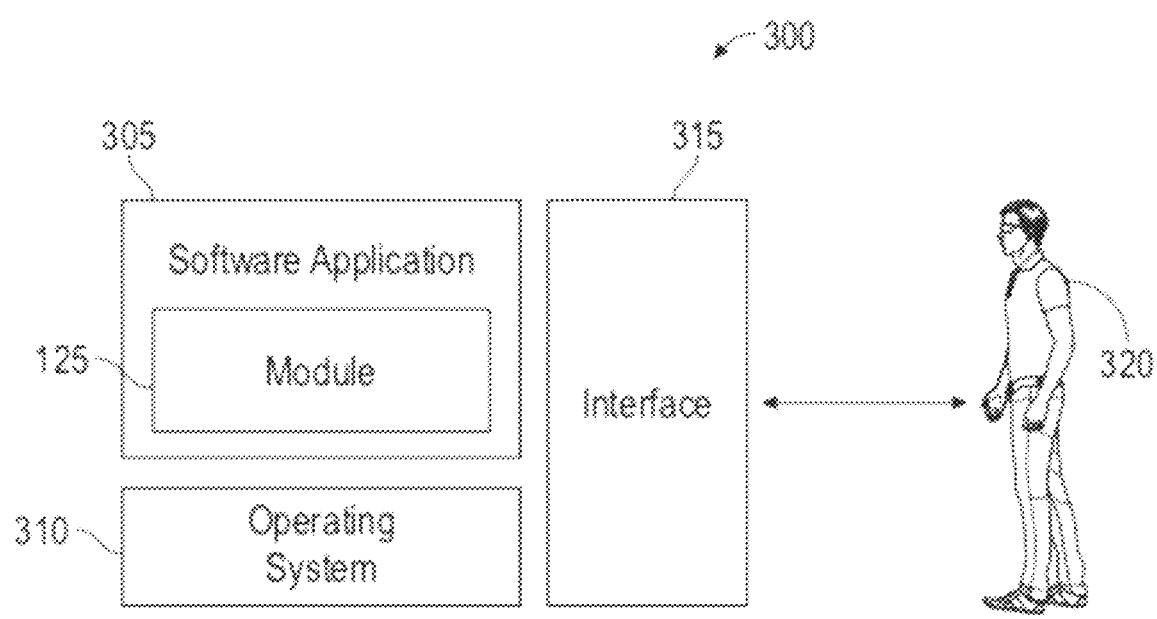
FIG. 3 depicts a computer software system for directing the operation of the data-processing system depicted in FIG. 1, in accordance with an example embodiment.

FIGS. 1-3 are provided as exemplary diagrams of data-processing environments in which embodiments of the present invention may be implemented. It should be appreciated that FIGS. 1-3 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

A block diagram of a computer system 100 that executes programming for implementing parts of the methods and systems disclosed herein is shown in FIG. 1. A computing device in the form of a computer 110 configured to interface with controllers, peripheral devices, and other elements disclosed herein may include one or more processing units 102, memory 104, removable storage 112, and non-removable storage 114. Memory 104 may include volatile memory 106 and non-volatile memory 108. Computer 110 may include or have access to a computing environment that includes a variety of transitory and non-transitory computer-readable media such as volatile memory 106 and non-volatile memory 108, removable storage 112 and non-removable storage 114. Computer storage includes, for example, random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage, or other magnetic storage devices, or any other medium capable of storing computer-readable instructions as well as data including image data.

Computer 110 may include, or have access to, a computing environment that includes input 116, output 118, and a communication connection 120. The computer may operate in a networked environment using a communication connection 120 to connect to one or more remote computers, remote sensors and/or controllers, detection devices, hand-held devices, multi-function devices (MFDs), speakers, mobile devices, tablet devices, mobile phones, Smartphone, or other such devices. The remote computer may also include a personal computer (PC), server, router, network PC, RFID enabled device, a peer device or other common network node, or the like. The communication connection may include a Local Area Network (LAN), a Wide Area Network (WAN), Bluetooth connection, or other networks. This functionality is described more fully in the description associated with FIG. 2 below.

Output 118 is most commonly provided as a computer monitor, but may include any output device. Output 118 and/or input 116 may include a data collection apparatus associated with computer system 100. In addition, input 116, which commonly includes a computer keyboard and/or pointing device such as a computer mouse, computer track pad, or the like, allows a user to select and instruct computer system 100. A user interface can be provided using output 118 and input 116. Output 118 may function as a display for displaying data and information for a user, and for interactively displaying a graphical user interface (GUI) 130.

Note that the term "GUI" generally refers to a type of environment that represents programs, files, options, and so forth by means of graphically displayed icons, menus, and dialog boxes on a computer monitor screen. A user can interact with the GUI to select and activate such options by directly touching the screen and/or pointing and clicking with a user input device 116 such as, for example, a pointing device such as a mouse, and/or with a keyboard. A particular item can function in the same manner to the user in all applications because the GUI provides standard software routines (e.g., module 125) to handle these elements and report the user's actions. The GUI can further be used to display the electronic service image frames as discussed below.

Computer-readable instructions, for example, program module or node 125, which can be representative of other modules or nodes described herein, are stored on a computer-readable medium and are executable by the processing unit 102 of computer 110. Program module or node 125 may include a computer application. A hard drive, CD-ROM, RAM, Flash Memory, and a USB drive are just some examples of articles including a computer-readable medium.

FIG. 2 depicts a graphical representation of a network of data-processing systems 200 in which aspects of the present invention may be implemented. Network data-processing system 200 can be a network of computers or other such devices, such as mobile phones, smartphones, sensors, controllers, speakers, tactile devices, and the like, in which embodiments of the present invention may be implemented. Note that the system 200 can be implemented in the context of a software module such as program module 125. The system 200 includes a network 202 in communication with one or more clients 210, 212, and 214. Network 202 may also be in communication with one or more devices 204, servers 206, and storage 208. Network 202 is a medium that can be used to provide communications links between various devices and computers connected together within a networked data processing system such as computer system 100. Network 202 may include connections such as wired communication links, wireless communication links of various types, and fiber optic cables. Network 202 can communicate with one or more servers 206, one or more external devices such as device 204, and a memory storage unit such as, for example, memory or database 208. It should be understood that device 204 may be embodied as a NMR device as disclosed herein.

In the depicted example, device 204, server 206, and clients 210, 212, and 214 connect to network 202 along with storage unit 208. Clients 210, 212, and 214 may be, for example, personal computers or network computers, handheld devices, mobile devices, tablet devices, smartphones, personal digital assistants, printing devices, recording devices, speakers, MFDs, etc. Computer system 100 depicted in FIG. 1 can be, for example, a client such as client 210 and/or 212 and/or 214.

Computer system 100 can also be implemented as a server such as server 206, depending upon design considerations. In the depicted example, server 206 provides data such as boot files, operating system images, applications, and application updates to clients 210, 212, and/or 214. Clients 210, 212, and 214 and device 204 are clients to server 206 in this example. Network data-processing system 200 may include additional servers, clients, and other devices not shown. Specifically, clients may connect to any member of a network of servers, which provide equivalent content.

In the depicted example, network data-processing system 200 is the Internet, with network 202 representing a worldwide collection of networks and gateways that use the Transmission Control Protocol/Internet Protocol (TCP/IP) suite of protocols to communicate with one another. At the heart of the internet is a backbone of high-speed data communication lines between major nodes or host computers consisting of thousands of commercial, government, educational, and other computer systems that route data and messages. Of course, network data-processing system 200 may also be implemented as a number of different types of networks such as, for example, an intranet, a local area network (LAN), or a wide area network (WAN). FIGS. 1 and 2 are intended as examples and not as architectural limitations for different embodiments of the present invention.

FIG. 3 illustrates a software system 300, which may be employed for directing the operation of the data-processing systems such as computer system 100 depicted in FIG. 1. Software application 305, may be stored in memory 104, on removable storage 112, or on non-removable storage 114 shown in FIG. 1, and generally includes and/or is associated with a kernel or operating system 310 and a shell or interface 315. One or more application programs, such as module(s) or node(s) 125, may be "loaded" (i.e., transferred from removable storage 112 into the memory 104) for execution by the data-processing system 100. The data-processing system 100 can receive user commands and data through user interface 315, which can include input 116 and output 118, accessible by a user 320. These inputs may then be acted upon by the computer system 100 in accordance with instructions from operating system 310 and/or software application 305 and any software module(s) 125 thereof.

Generally, program modules (e.g., module 125) can include, but are not limited to, routines, subroutines, software applications, programs, objects, components, data structures, etc., that perform particular tasks or implement particular abstract data types and instructions. Moreover, those skilled in the art will appreciate that elements of the disclosed methods and systems may be practiced with other computer system configurations such as, for example, handheld devices, mobile phones, smartphones, tablet devices, multi-processor systems, microcontrollers, printers, copiers, fax machines, multi-function devices, data networks, microprocessor-based or programmable consumer electronics, networked personal computers, minicomputers, mainframe computers, servers, medical equipment, medical devices, and the like.

Note that the term "module" or "node" as utilized herein may refer to a collection of routines and data structures that perform a particular task or implements a particular abstract data type. Modules may be composed of two parts: an interface, which lists the constants, data types, variables, and routines that can be accessed by other modules or routines; and an implementation, which is typically private (accessible only to that module) and which includes source code that actually implements the routines in the module. The term module may also simply refer to an application such as a computer program designed to assist in the performance of a specific task such as word processing, accounting, inventory management, etc., or a hardware component designed to equivalently assist in the performance of a task.

The interface 315 (e.g., a graphical user interface 130) can serve to display results, whereupon a user 320 may supply additional inputs or terminate a particular session. In some embodiments, operating system 310 and GUI 130 can be implemented in the context of a "windows" system. It can be appreciated, of course, that other types of systems are possible. For example, rather than a traditional "windows" system, other operation systems such as, for example, a real-time operating system (RTOS) more commonly employed in wireless systems may also be employed with respect to operating system 310 and interface 315. The software application 305 can include, for example, module(s) 125, which can include instructions for carrying out steps or logical operations such as those shown and described herein.

The following description is presented with respect to embodiments of the present invention, which can be embodied in the context of, or require the use of, a data-processing system such as computer system 100, in conjunction with program module 125, and data-processing system 200 and network 202 depicted in FIGS. 1-3. The present invention, however, is not limited to any particular application or any particular environment. Instead, those skilled in the art will find that the system and method of the present invention may be advantageously applied to a variety of system and application software including database management systems, word processors, and the like. Moreover, the present invention may be embodied on a variety of different platforms including Windows, Macintosh, UNIX, LINUX, Android, Arduino, and the like. Therefore, the descriptions of the exemplary embodiments, which follow, are for purposes of illustration and not considered a limitation.

In an embodiment, a system and method for optimized, non-invasive measurement of nuclear magnetic resonance (NMR) relaxometry signals from the distal end of a human finger are disclosed. The embodiments can be used to monitor an individual's metabolic health by measuring $T_2$ or $T_1$ relaxation times of tissues in the fingertip. It should be understood that $T_2$ relaxation time is a powerful and practical biomarker for monitoring cardio-metabolic health, and detecting, for example, early risk for type 2 diabetes and atherosclerotic cardiovascular disease.

Early detection and intervention is the best way to prevent type 2 diabetes and cardiovascular disease. The methods and systems disclosed herein can provide metabolic health screening in point-of-care settings, like primary care medical clinics. The embodiments are non-invasive and do not require a blood sample.

In the embodiments disclosed herein, a "sample" used for NMR relaxometry analysis can be non-invasively taken from the finger (e.g., an index finger, but other fingers could also be used) of a living human being, as opposed to a liquid substance inside of a glass tube. The systems disclosed can generate a profile of the physical and dynamical properties of the molecules in the sample (i.e. the patient's finger). Changes in the motion of the molecules in the sample can be equated with changes in metabolism or metabolic health.

In an embodiment, an NMR relaxometry system can comprise a housing, a testing assembly in the housing, and a computer or other such device for reading out results of a test.

Figure 4:
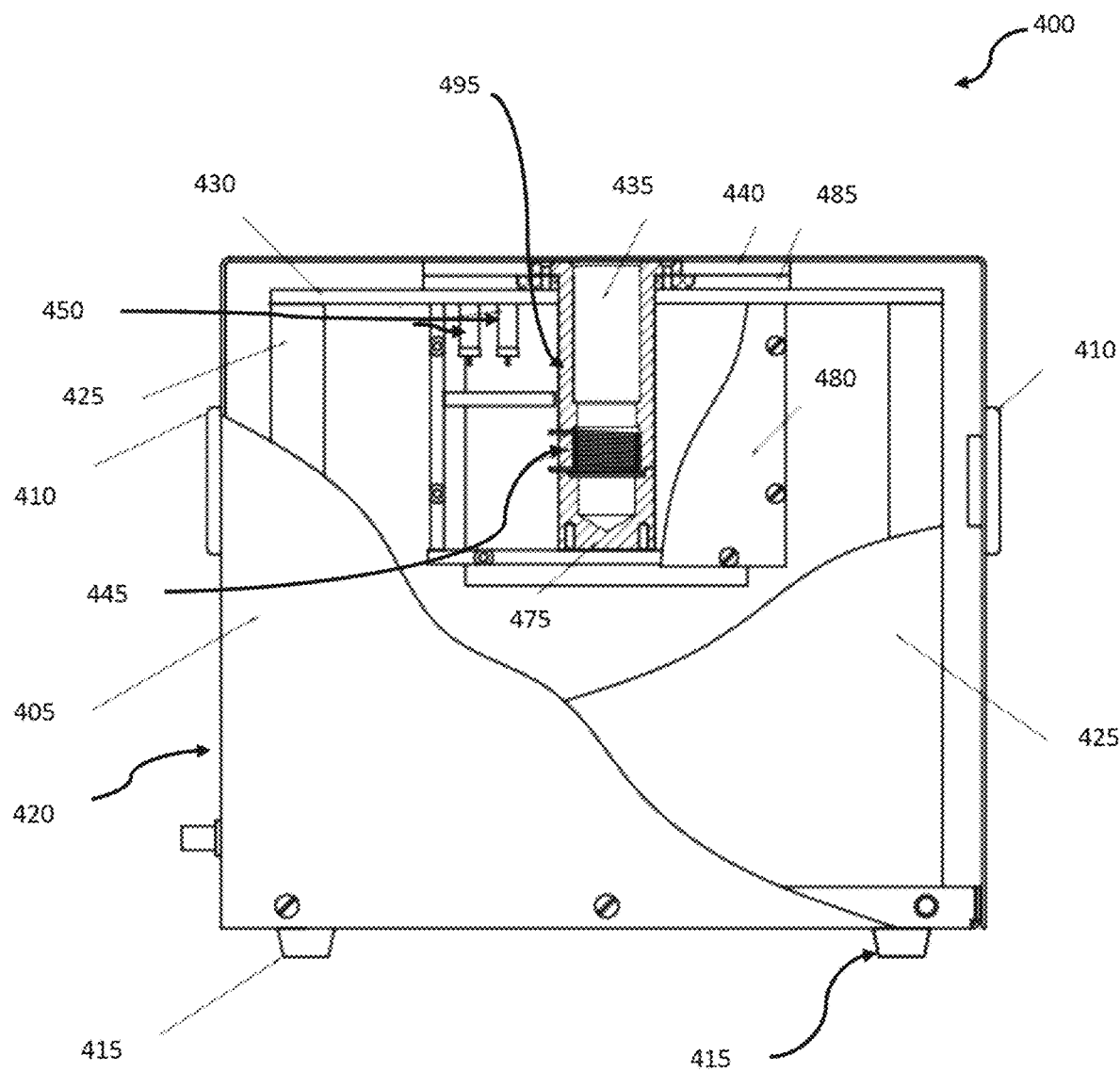
FIG. 4 depicts an NMR device for measuring metabolic health in accordance with the disclosed embodiments.

FIG. 4 illustrates a system 400 for NMR relaxometry measurement of metabolic health. The housing can include a container formed by a magnet cover 405. The magnet cover 405 surrounds a permanent magnet 450, a heater element coupled electronically to an external temperature regulator (to keep the magnetic field stable), and a probe 495. The probe 495 sits in between the north and south poles of the magnet 450 and serves as the interface between the magnet 450, the transceiver coils 445 and the sample (i.e., a human finger). The probe 495 can be cylindrical in shape, designed with a diameter to accommodate an average sized human finger (e.g., 20.5 mm, but other diameters can be used in other embodiments).

The magnet cover 405, or body 420, houses the permanent magnet 450. The permanent magnet 450 provides a nearly homogeneous magnetic field across the volume of the probe 495 and, by extension, the test subject's fingertip. The magnetic field must be nearly homogenous at the proper depth from the top of the magnet box in order to provide accurate readings. Any remaining field inhomogeneity can be eliminated using a Carr-Purcell-Meiboom-Gill (CPMG) pulse sequence to collect $T_2$ values. Accordingly, the permanent magnet 450 provides a homogeneous magnetic field specifically tailored to the geometry of a typical human hand. Thus, the critical region of the magnetic field is larger and closer to the top surface. The two magnet blocks 450 and a pole shoes can be placed below the edge of the magnet yoke 425. This is necessary to provide the optimal depth of the probe 495 to accommodate a human fingertip within the homogeneous magnetic field region, or "sweet spot".

The body 420 of the system 400 can include one or more handles 410 that can be provided on the exterior of the body 420. The body 420 generally includes sidewalls and a top and bottom surface, thereby enclosing the various components of the system 400. One or more standoffs 415 can be formed on the bottom surface of the body 420, which serve to hold the body 420 off the surface on which the system 400 is sitting.

The system includes a cover 430, which can be formed of plastic, or other such non-magnetic material, and is configured near the top side of the body 420 and extends from the sidewalls along the inside of the body, with a void where the NMR coil holder 435 is formed. The NMR coil holder 435 can comprise a poly tetrafluoroethylene (PTFE) NMR coil holder or can be comprised of other, similar materials. A plastic frame 440 can be fitted to the cover 430 and/or the PTFE NMR coil holder 435 to secure the PTFE NMR coil holder in position near the top of the body 420.

The NMR coil 445 is configured below the PTFE NMR coil holder 435, and on a NMR coil base 475, collectively known as the NMR coil assembly. The coil base 475 can also be a PTFE NMR coil base or can be formed of other similar material. HV capacitors 485, used to tune the circuit to the proper resonance frequency and impedance, are attached to the cover 430 in proximity to the PTFE NMR coil holder 435. The coil assembly is covered by a cover assembly 480 that can be formed of brass or other such materials.

Figure 5:
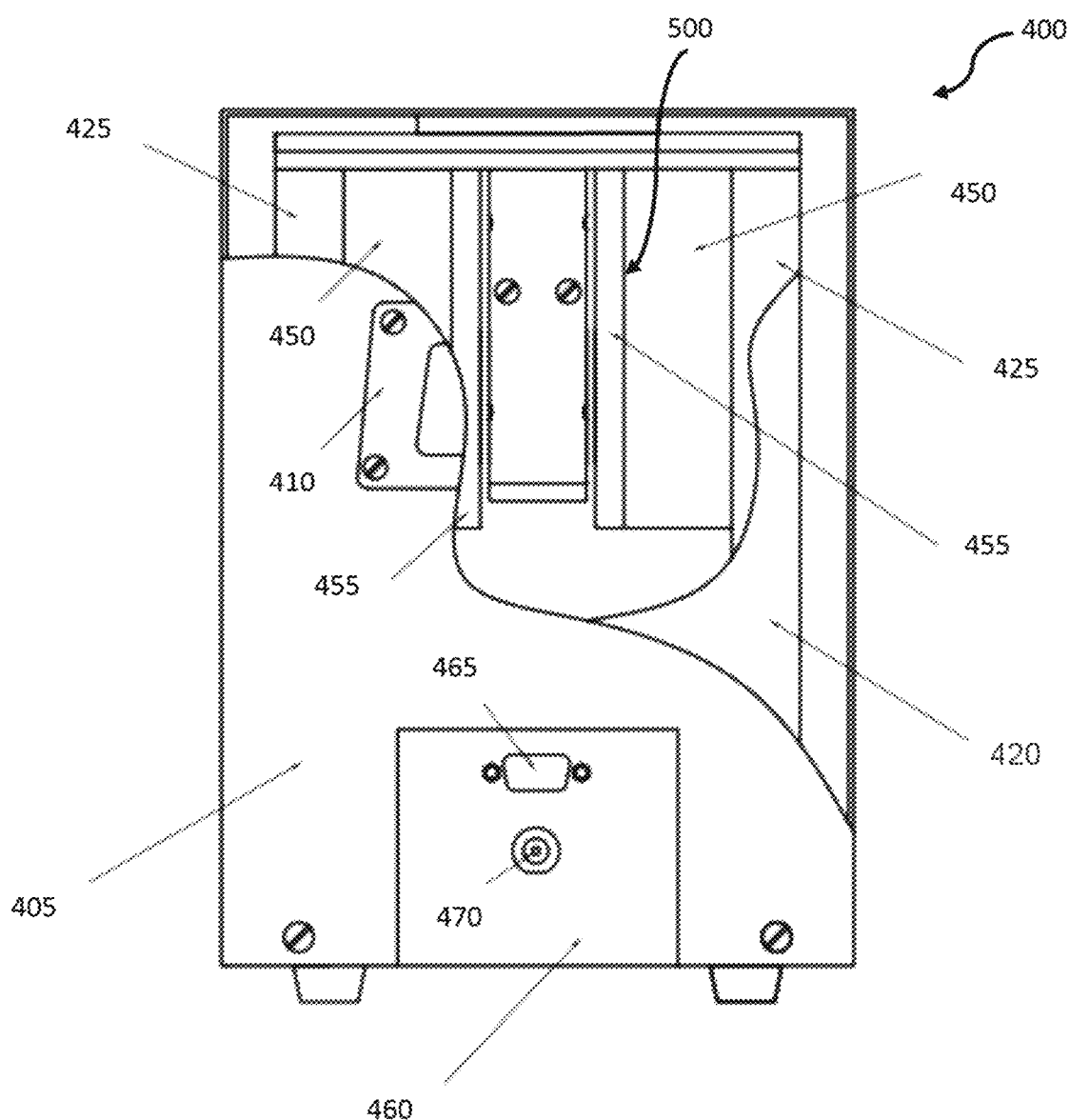
FIG. 5 depicts an NMR device for measuring metabolic health in accordance with the disclosed embodiments.

The sensor probe head assembly 500, illustrated in FIG. 5, has a case that can be formed with aluminum or other similar material.

The system 400 is further illustrated in FIG. 5, where a magnet assembly, including the permanent magnet 450, is connected to a magnet pole shoe 455, just exterior to the PTFE NMR coil holder 435. The permanent magnet 450 can comprise two blocks (which can be rectangular in some embodiments) made of a rare earth magnet, including the rare earth material Neodymium, or other such powerful permanent magnetic material. In an embodiment, the material can comprise N42, which refers to a grade of neodymium-iron-boron, or NdFeB. The dimensions of the magnet blocks can be sized to provide the desired magnetic field. In certain embodiments, this can be 100×100×30 mm, but other dimensions may be necessary according to design considerations.

The magnet assembly includes pole shoes 455, which serve to support the magnet blocks 450 and disperse the magnetic field with the desired directionality. The pole shoes 455 can be made, for example, of soft magnetic steel, polished, and annealed at 600 degrees C. in a nitrogen atmosphere, to eliminate mechanical internal strains. Other pole shoes that provide a similar dispersion of the magnetic field can also be used.

The two magnet blocks 450 and pole shoes 455 can be placed 5-10 mm lower than the edge of the magnet yoke 425. This is necessary to provide the optimal depth of the probe 495 to accommodate a human fingertip within the homogeneous magnetic field region or "sweet spot".

Figure 8:
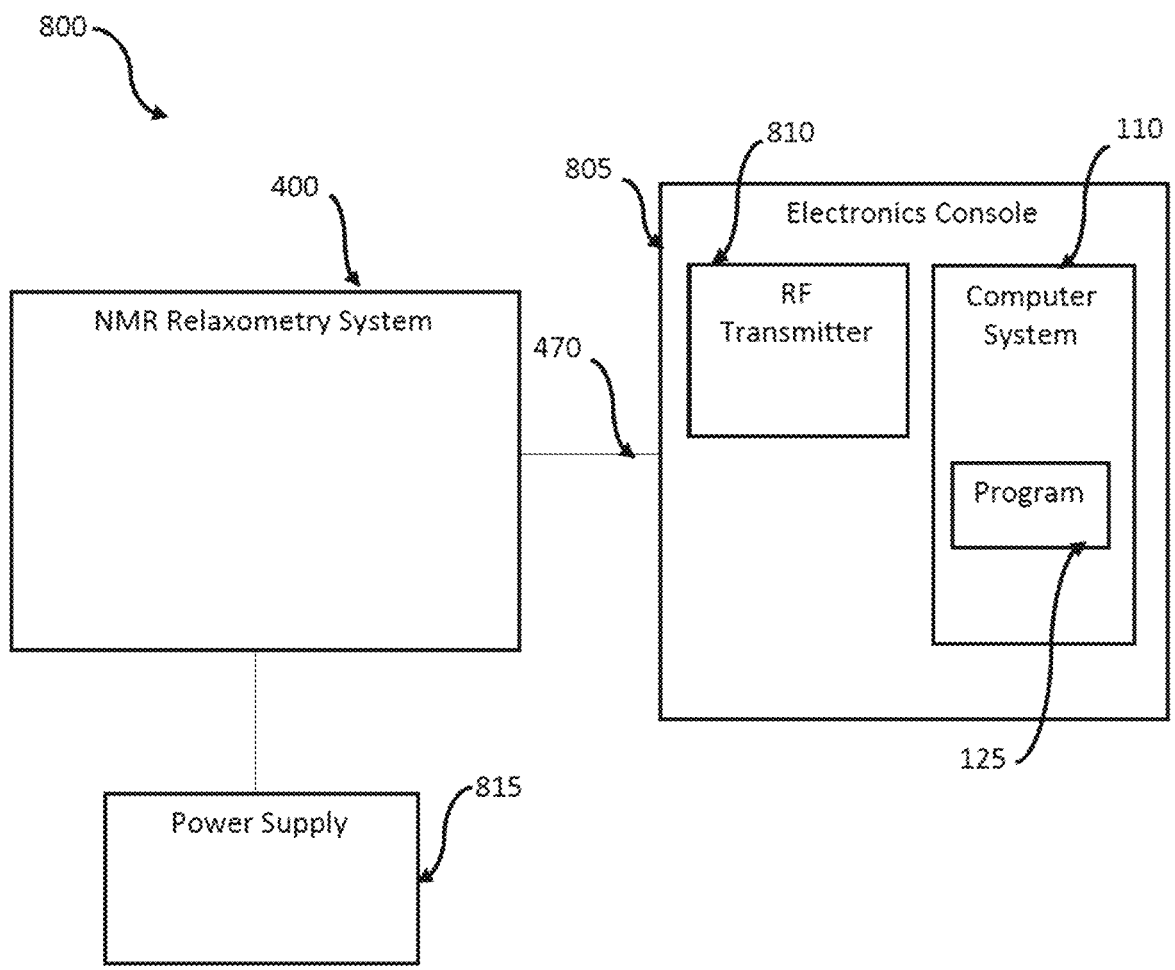
FIG. 8 depicts a block diagram of a system for measuring metabolic health in accordance with the disclosed embodiments.

The magnet assembly can be thermally insulated, by an insulator if necessary, and housed within a stainless steel outer shell or body 420. The temperature stability of the magnet is achieved with a standard temperature controller connected to one or more heaters (preferably providing unto to 24 watts), and a standard temperature sensor. It should be understood that the temperature controller can be embodied as software associated with a computer system operably connected to the system 400 as illustrated in FIG. 8. FIG. 5 further illustrates a connector panel 460. The connector panel 460 includes a heater connection 465 that provides connection to the heater.

An RF connection 470 is provided on the connector panel 460. The RF connection 470 can be connected to an external electronics console, which houses an RF transmitter and receiver electronics and an acquisition computer, as further detailed in FIG. 8. This connector couples the NMR probe electronics inside the magnet box with the exterior electronics console.

The connector panel 460 can further provide connections to various external devices such as a power supply and/or battery, and a host computer that provides the interface to the user. The user interacts with the instrument through software that implements the NMR pulse sequence, collects data, and analyzes the collected data.

Figure 6:
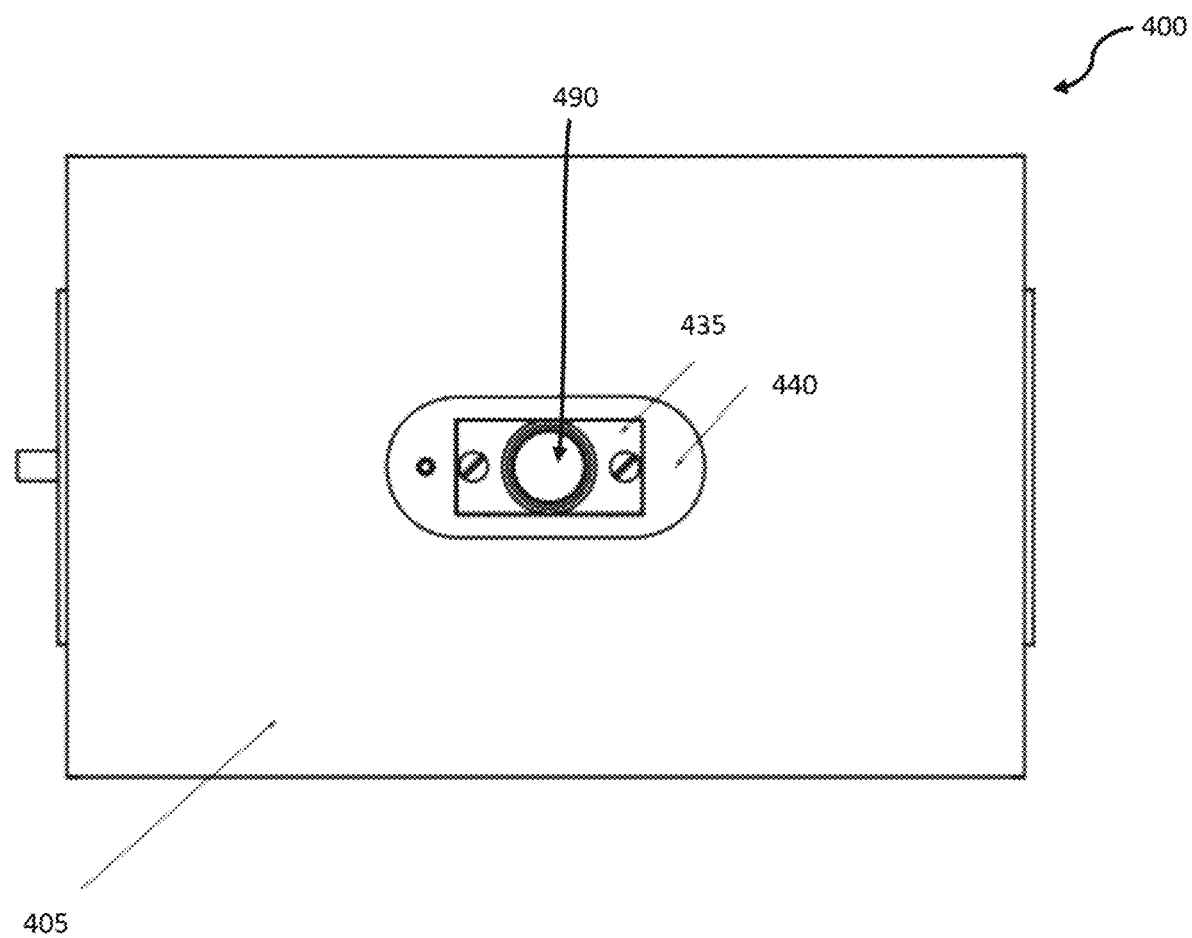
FIG. 6 depicts a top view of an NMR device for measuring metabolic health in accordance with disclosed embodiments.

A top view of the system 400 is illustrated in FIG. 6. The top of the system 400 includes a hole 490, where a test subject's finger can be inserted into the testing space formed in the plastic frame 440 by the PTFE NMR coil holder 435, NMR coil 445, and the PTFE NMR coil base 475. The top view illustrates the top cover, comprising the magnet cover 405.

Figure 7:
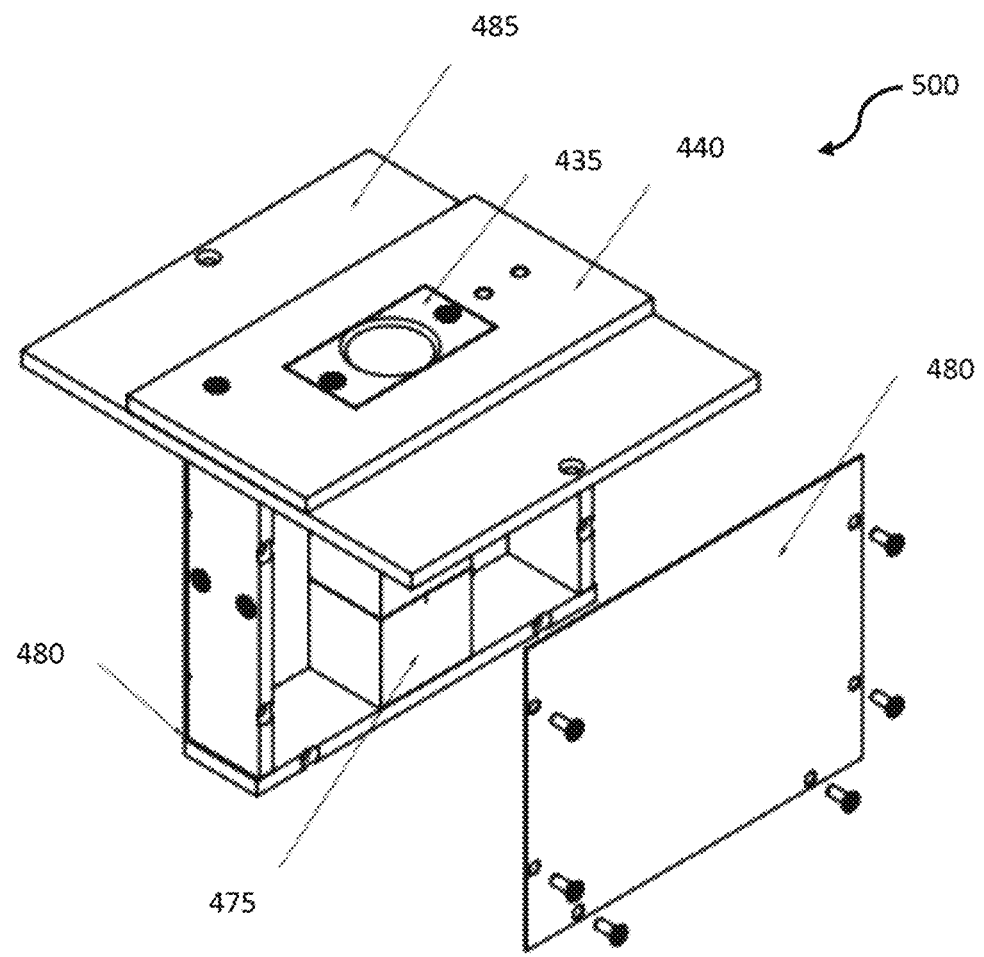
FIG. 7 depicts a sensor probe head assembly associated with an NMR device for measuring metabolic health in accordance with the disclosed embodiments.

FIG. 7 illustrates a more detailed view of the sensor probe head assembly 500. The sensor probe head assembly 500 includes the sensor probe head case 485 upon which the PTFE NMR coil holder 430 and plastic frame 440 are mounted. The surrounding cover 480 is illustrated (detached from the assembly 500 for clarity). At the bottom of the assembly, the PTFE coil holder 475 is illustrated.

FIG. 8 illustrates a block diagram of a system 800 in accordance with the disclosed embodiments. The system 800 includes the system 400, as described herein, that uses NMR relaxometry analysis to non-invasively sample the finger of a living human being (e.g., without a needle stick) to generate a profile of the physical and dynamical properties of the molecules in the sample (i.e., the patient's finger).

The RF connection 470 from the system (provided on the connector panel 460) can be connected to an external electronics console 805, which houses an RF transmitter 810. The RF transmitter 810 can include receiver electronics and an acquisition computer, which can be embodied as a computer system such as computer system 110. The connector 470 couples the NMR probe electronics inside the magnet box as described in system 400 with the electronics console 805. In other embodiments, the system 800 can be integrated in a single housing or unit.

The connector panel 460 can further provide connection to various external devices such as a power supply 815, which can be embodied as a wall outlet, battery, or other such power supply.

The integrated computer system 110, or a separate computing device, can provide an interface to the user. The user interacts with the instrument through a software module 125 and GUI. The software module 125 implements the NMR pulse sequence via the RF transmitter 810, collects data from the system 400, and analyzes that data as further disc used herein.

A key aspect of the disclosed embodiments is the ability to collect NMR relaxometry data on a living human finger and resolve several $T_2$ values representing different tissue elements. In certain embodiments, analysis of isolated non-living tissues can be used as control samples. It should be understood that the dominant components observed in the $T_2$ profile of the living finger arise from adipose tissue.

Figure 9A:
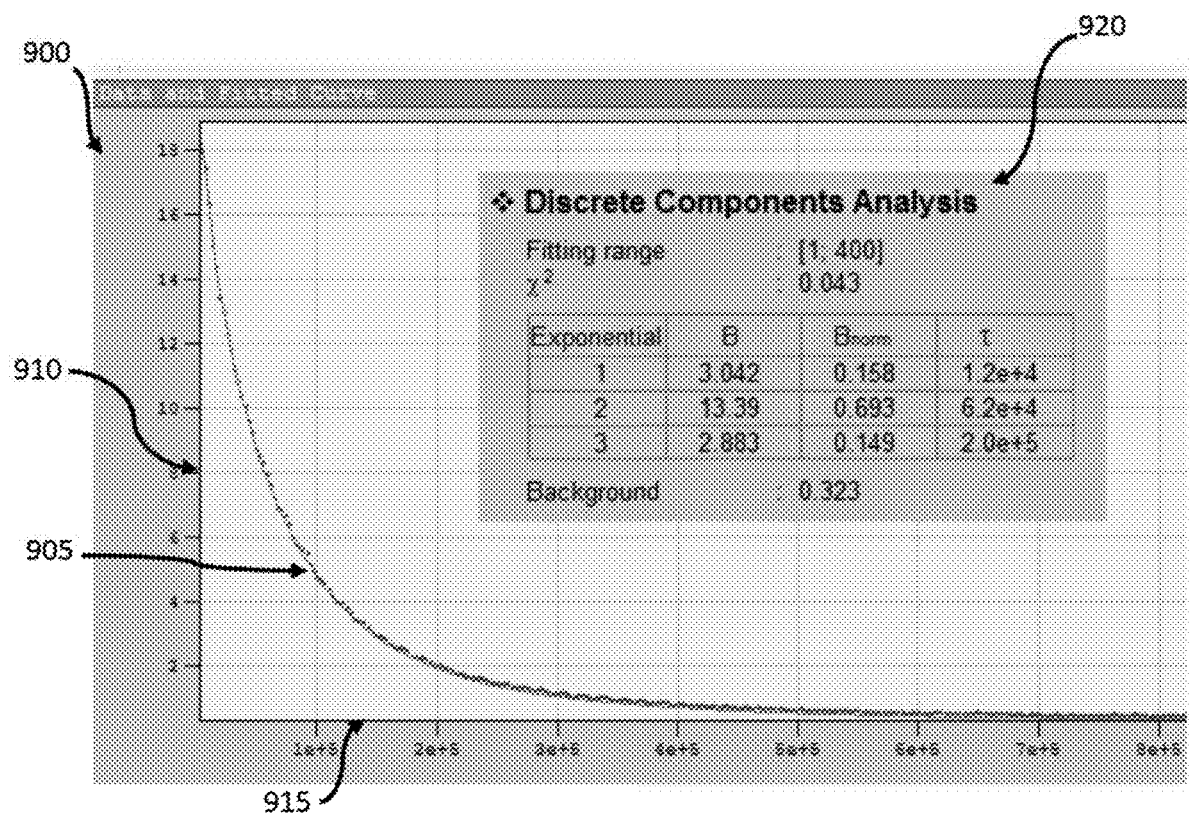
FIG. 9A depicts a chart illustrating output from an NMR device for measuring metabolic health, in accordance with the disclosed embodiments.

NMR relaxometry data is acquired on a living human finger according to the methods and systems disclosed herein. FIG. 9A illustrates a chart 900 of data that can be collected and provided to a medical practitioner according to the methods and systems disclosed. Specifically, plot 905 is a Carr-Purcell-Meiboom-Gill (CPMG) $T_2$ decay curve. In certain embodiments, this data can be acquired with system 400 in approximately 1 minute or less.

The y-axis 910 represents NMR signal intensity (i.e., the output voltage) and the x-axis 915, illustrates decay time. A discrete inverse Laplace transform can be applied to the decay curve in order to extract three individual $T_2$ components. The inset 920 indicates the relative intensity ($B_{norm}$) and $T_2$ value (tau, in microseconds) for each of the three components.

Figure 9B:
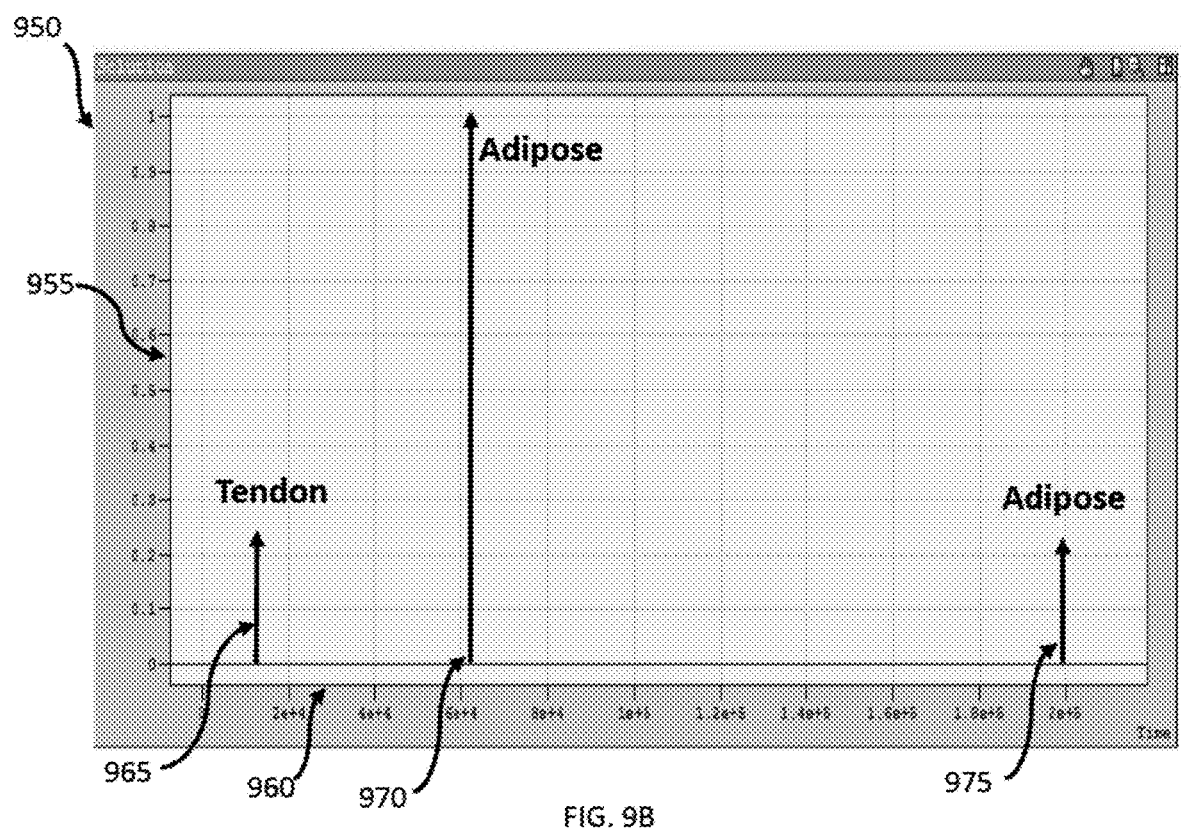
FIG. 9B depicts a chart illustrating output from an NMR device for measuring metabolic health in accordance with the disclosed embodiments.

FIG. 9B illustrates chart 950 which graphically depicts the results of the discrete inverse Laplace transform, showing the distribution of the three $T_2$ components. The y-axis 955 is relative NMR signal intensity ($B_{norm}$), and the x-axis 960 is $T_2$. The dominant contributor to the left-most peak 965 is tendon, while the dominant contributor to the middle peak 970 and right-most peak 975 is adipose tissue. The position of these three peaks on the x-axis 960 is indicative of the fluidity of that component. The higher the $T_2$ value, the higher the tissue fluidity. Adipose tissue yields two $T_2$ components representing different mobility domains within that tissue.

The analysis results are thus displayed in the form of an increasing or decaying exponential signal as a function of decay time, as illustrated in FIGS. 9A and 9B. As such, according to the method disclosed herein, collection of hundreds or thousands of data points per decay curve are possible, which provides the ability to conduct more sophisticated multi-exponential fitting with 3 or 4 components. In certain embodiments, the algorithm used for such fitting can be a discrete inverse Laplace transform but other algorithms can also be used. According to the methods and systems disclosed herein resolution of up to four tissue compartments, such as tendon, adipose tissue, blood and lymph, is possible.

Figure 10:
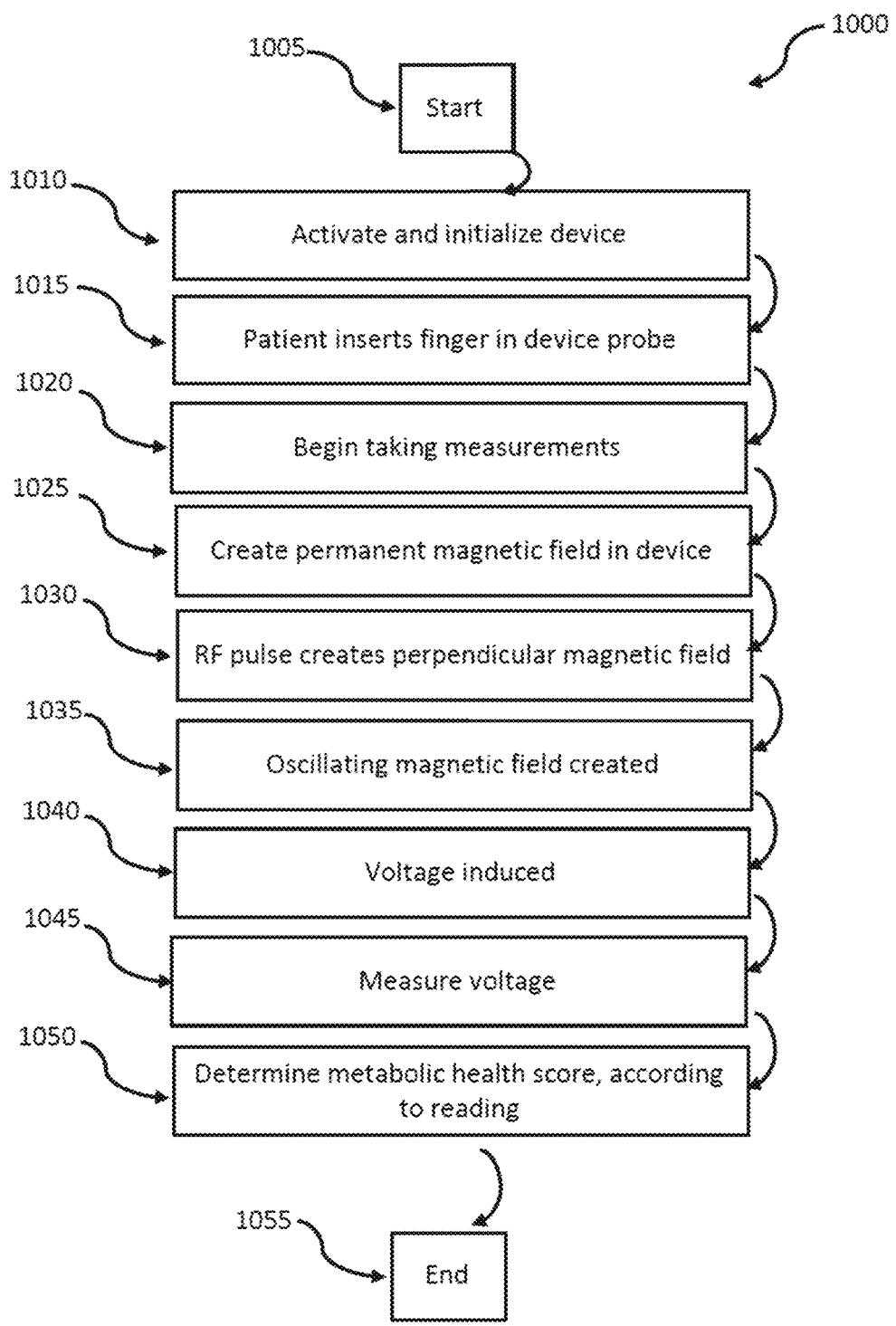
FIG. 10 depicts a flow chart of steps associated with a method for measuring metabolic health in accordance with the disclosed embodiments.

FIG. 10 illustrates a flow chart associated with a method 1000 for measuring metabolic health, according to relaxation variables, using the systems and apparatuses described herein. The method begins at step 1005. At step 1010, the NMR device 400 and/or system 800 can be activated. Next, at step 1015, the patient can insert their finger through a hole into the probe of the device 400. At this point, the device is ready and the process of taking measurement can begin as illustrated at step 1020.

In general, the device functions by introducing the subject's finger to the magnetic field created in the device by permanent magnets as shown at step 1025. The magnetic field aligns the magnetic moments of hydrogen atoms in the subject's finger (most notably the hydrogen in the adipose tissue in the subject's finger) with (or against) the permanent magnetic field.

At step 1030, a radio frequency pulse can then be applied in a direction that provides a secondary magnetic field perpendicular to the permanent magnetic field. This temporarily changes the magnetic moment of the hydrogen atoms away from their equilibrium state. The change in the magnetic moment, away from equilibrium, is determined by the duration of the pulse. The combined realignment of the hydrogen atoms back to their equilibrium state generates a small oscillating or non-oscillating magnetic field as shown at step 1035. The changing magnetic field in turn induces an alternating voltage in the coil surrounding the subject's finger as shown at step 1040, which can be measured and reported with a computer, oscilloscope, or other such device as shown at step 1045. The rate of increase or decay of the voltage can then be equated to a $T_1$ or $T_2$ value, which can be used to determine metabolic health at step 1050. The method ends at step 1055.

Adipose tissue contains cells (adipocytes) filled with internal lipid droplets, as well as a fibrous extracellular matrix to provide mechanical support, and blood vessels and other immune cells. As the tissue becomes more fluid, the $T_2$ value increases. By contrast, more rigidity in the tissue results in a lowering of the $T_2$. These changes in tissue fluidity occur with changes in metabolism and metabolic health.

Using to the methods and systems disclosed herein, adipose tissue yields the largest signal. This is a result of the fact that adipose tissue constitutes the largest percentage of the tissue in the distal phalanx of the finger and because it is relatively fluid. Adipose tissue fluidity (monitored as adipose tissue $T_2$) is an important measure of metabolic health and disease risk. In part, adipose $T_2$ reflects the fatty acid composition of the stored lipids. For example, an individual consuming large amounts of fish or fish oil will have a more fluid adipose tissue and a higher $T_2$ value compared with those consuming a diet rich in saturated fats. Furthermore, $T_2$ is exquisitely sensitive to lipid fluidity, especially as it pertains to omega-3 content.

Adipose tissue fluidity is also important with respect to inflammation and fibrosis. Adipose tissue inflammation is a key driver of early metabolic syndrome—the early metabolic abnormalities that put someone at risk for type 2 diabetes and cardiovascular disease. Adipose tissue fibrosis, which makes the tissue more rigid, is associated with inflammation and would drive the $T_2$ value lower.

Accordingly, the disclosed methods, systems, and devices can screen for early metabolic syndrome. Specifically, the embodiments provide a non-invasive, fingertip assessment of metabolic health, measured in about a minute. High adipose $T_2$ and high adipose tissue fluidity is indicative of better metabolic health and lower risk of diabetes or cardiovascular disease. By contrast, low adipose $T_2$ is indicative of poor metabolic health. $T_2$ is a marker of adipose tissue inflammation and early metabolic syndrome, where low adipose $T_2$ also reflects a diet high in saturated fats and low in fish/fish oil. Such diets are associated with increased diabetes and cardiovascular risk.

Based on the foregoing, it can be appreciated that a number of embodiments, preferred and alternative, are disclosed herein. For example, in one embodiment, a medical testing system comprises a housing, at least one magnet assembly configured around a probe configured to accept a human finger, formed in said housing wherein said at least one magnet assembly creates a permanent magnetic field around said probe, an RF signal generator configured to create a temporary magnetic field perpendicular to said permanent magnetic field in said housing, and an NMR coil assembly wherein a change in said permanent magnetic field induces a voltage in said NMR coil assembly.

In an embodiment, the NMR coil assembly further comprises an NMR coil surrounding said probe and a coil base configured to hold said NMR coil. In an embodiment, the at least one magnet assembly further comprises a permanent magnet mounted in said housing externally to said probe. In another embodiment, the permanent magnet further comprises a rare earth magnet. In another embodiment, the at least one magnet assembly further comprises a yoke and a magnet pole shoe configured to disperse said permanent magnetic field.

In an embodiment, the medical testing system further comprises a heater configured inside said housing wherein said heater maintains a temperature inside said housing.

In an embodiment, the medical testing system further comprises an output operably connected to said NMR coil assembly wherein said output comprises a non-invasive measurement of at least one of $T_2$ and $T_1$ in intact living tissue indicative of at least one of adipose tissue fluidity and metabolic health.

In an embodiment, the an apparatus comprises a housing, at least one magnet assembly configured around a probe configured to accept a human finger, formed in said housing wherein said at least one magnet assembly creates a permanent magnetic field around said probe, an RF signal generator configured to create a temporary magnetic field perpendicular to said permanent magnetic field in said housing, and an NMR coil assembly wherein a change in said permanent magnetic field induces a voltage in said NMR coil assembly.

In an embodiment, the NMR coil assembly further comprises an NMR coil surrounding said probe and a coil base configured to hold said NMR coil. In an embodiment, the at least one magnet assembly further comprises a permanent magnet mounted in said housing externally to said probe. In an embodiment, the permanent magnet further comprises a rare earth magnet. In an embodiment, the at least one magnet assembly further comprises a yoke and a magnet pole shoe configured to disperse said permanent magnetic field.

In an embodiment, the apparatus comprises a heater configured inside said housing wherein said heater maintains a temperature inside said housing.

In an embodiment, the apparatus comprises an output operably connected to said NMR coil assembly wherein said output comprises a non-invasive measurement of at least one of $T_2$ and $T_1$ in intact living tissue indicative of at least one of: adipose tissue fluidity and metabolic health.

In yet another embodiment, a medical testing method comprises initializing an NMR testing device, inserting a test subject's finger into a test probe, said test probe configured between at least one magnet assembly configured formed in said NMR testing device, generating a permanent magnetic field around said probe, creating a temporary magnetic field perpendicular to said permanent magnetic field in said housing with an RF signal generator, and measuring an induced voltage in an NMR coil assembly resulting from a change in said permanent magnetic field.

In an embodiment of the method, the NMR coil assembly further comprises an NMR coil surrounding said probe and a coil base configured to hold said NMR coil. In an embodiment of the method, the at least one magnet assembly further comprises a permanent magnet mounted in said housing externally to said probe. In an embodiment, the method further comprises dispersing said permanent magnetic field with a magnet pole shoe.

In an embodiment, the method further comprises maintaining a temperature inside said NMR testing device with a heater.

In an embodiment, the method further comprises outputting a non-invasive measurement of at least one of $T_2$ and $T_1$ in intact living tissue indicative of at least one of: adipose tissue fluidity and metabolic health.

It will be appreciated that variations of the above-disclosed and other features and functions, or alternatives thereof, may be desirably combined into many other different systems or applications. Also, it should be understood that various presently unforeseen or unanticipated alternatives, modifications, variations or improvements therein may be subsequently made by those skilled in the art which are also intended to be encompassed by the following claims.

What is claimed is:

1. A medical testing system comprising:
   a housing comprising a magnet cover, a thermal insulator, and a shell;
   at least one magnet assembly comprising:
   two magnets comprising a first magnet and a second magnet configured around a probe, said probe configured to accept a human finger;
   a first magnet pole shoe configured external to, and between said first magnet and said probe, and a second magnet pole shoe configured external to, and between said second magnet and said probe; and
   a first magnet yoke associated with said first magnet and a second magnet yoke associated with said second magnet, wherein said two magnets, said first magnet pole shoe and said second magnet pole shoe are configured below an edge of each of said magnet yokes, wherein said at least one magnet assembly creates a permanent magnetic field around said probe and a homogeneous magnetic field at a desired depth in said probe;
   an RF signal generator configured to create a temporary magnetic field perpendicular to said permanent magnetic field in said housing;
   an NMR coil assembly comprising an NMR coil wrapped around said probe, a coil holder configured above said NMR coil, and a coil base configured below said NMR coil to hold said NMR coil; and
   an output operably connected to said NMR coil assembly wherein a change in said permanent magnetic field induces a voltage in said NMR coil assembly the induced voltage being indicative of a T2 measurement in adipose tissue in said human finger.

2. The medical testing system of claim 1 wherein said coil base is formed of poly tetrafluoroethylene and is configured to hold said NMR coil.

3. The medical testing system of claim 1 wherein said two magnets further comprise:
   permanent magnets mounted in said housing externally to said probe.

4. The medical testing system of claim 3 wherein said permanent magnets further comprise rare earth magnets.

5. The medical testing system of claim 1 wherein said two magnets and said magnet pole shoes configured below an edge of each of said magnet yokes associated with each of said two magnets create a sweet spot in said homogeneous magnetic field at said desired depth in said probe.

6. The medical testing system of claim 1 further comprising:
   a heater configured inside said housing wherein said heater maintains a temperature inside said housing.

7. The medical testing system of claim 1
   wherein said output comprises:
   a non-invasive measurement of T2 in intact living tissue indicative of adipose tissue fluidity and metabolic health.

8. An apparatus comprising:
   a housing comprising a magnet cover and a shell;
   at least one magnet assembly comprising:
   two magnets comprising a first magnet and a second magnet, said two magnets configured around a probe, said probe configured to accept a human finger;
   a first magnet pole shoe configured between said first magnet and said probe and a second magnet pole shoe configured between said second magnet and said probe; and
   a first magnet yoke associated with said first magnet and a second magnet yoke associated with said second magnet wherein said at least one magnet assembly creates a permanent magnetic field around said probe and a homogeneous magnetic field at a desired depth in said probe;
   an RF signal generator configured to create a temporary magnetic field perpendicular to said permanent magnetic field in said housing; and
   an NMR coil assembly comprising an NMR coil, a coil holder, and a coil base configured to hold said NMR coil;
   wherein a change in said permanent magnetic field induces a voltage in said NMR coil assembly the induced voltage being indicative of a T2 measurement in adipose tissue in said human finger.

9. The apparatus of claim 8 wherein said NMR coil is wrapped around said probe, said coil holder is configured above said NMR coil, and said coil base is configured to hold said NMR coil.

10. The apparatus of claim 8 wherein said two magnets further comprise:
    permanent magnets mounted in said housing externally to said probe.

11. The apparatus of claim 10 wherein said permanent magnets further comprise rare earth magnets.

12. The apparatus of claim 8 wherein said two magnets and each of said magnet pole shoes are configured below an edge of said yokes associated with each of said two magnets in order to create a sweet spot in said homogeneous magnetic field at said desired depth in said probe.

13. The apparatus of claim 8 further comprising:
    a heater configured inside said housing wherein said heater maintains a temperature inside said housing.

14. The apparatus of claim 8 further comprising:
    an output operably connected to said NMR coil assembly wherein said output comprises:
    a non-invasive measurement of T2 in intact living tissue in said human finger indicative of adipose tissue fluidity and metabolic health.

15. A medical testing method comprising:
    initializing an NMR testing device;
    inserting a test subject's finger into a test probe, said test probe configured between at least one magnet assembly formed in a housing comprising a magnet cover, an insulator, and a shell;
    generating a permanent magnetic field around said test probe with a magnet assembly comprising: two magnets comprising a first magnet and a second magnet, a first magnet pole shoe configured between said first magnet and said test probe, a second magnet pole shoe configured between said second magnet and said test probe, a first magnet yoke associated with said first magnet, and a second magnet yoke associated with said second magnet;
    creating a temporary magnetic field perpendicular to said permanent magnetic field in said housing with an RF signal generator; and measuring an induced voltage in an NMR coil assembly resulting from a change in said permanent magnetic field, the induced voltage being indicative of a T2 measurement in adipose tissue in said test subject's finger.

16. The medical testing method of claim 15 wherein said NMR coil assembly further comprises:
an NMR coil surrounding said test probe;
a coil holder configured above said NMR coil; and
a coil base configured to hold said NMR coil.

17. The medical testing method of claim 15 wherein said two magnets further comprise permanent magnets mounted in said housing externally to said test probe.

18. The medical testing method of claim 17 further comprising:
dispersing said permanent magnetic field with said magnet pole shoes.

19. The medical testing method of claim 15 further comprising:
maintaining a temperature inside said NMR testing device with a heater.

20. The medical testing method of claim 15 further comprising:
outputting a non-invasive measurement of the T2 measurement in intact living tissue indicative of: adipose tissue fluidity and metabolic health.

* * * * *